US00PP25358P3

(12) United States Plant Patent
Khemakongkanond

(10) Patent No.: US PP25,358 P3
(45) Date of Patent: Mar. 17, 2015

(54) ***AGLAONEMA* PLANT NAMED 'KKAG201303'**

(50) Latin Name: *Aglaonema commutatum*
Varietal Denomination: KKAG201303

(71) Applicant: Kanachana Khemakongkanond, Bangkok (TH)

(72) Inventor: Kanachana Khemakongkanond, Bangkok (TH)

( * ) Notice: Subject to any disclaimer, the term of this patent is extended or adjusted under 35 U.S.C. 154(b) by 162 days.

(21) Appl. No.: 13/815,838

(22) Filed: Mar. 15, 2013

(65) Prior Publication Data

US 2014/0283269 P1 Sep. 18, 2014

(51) Int. Cl.
*A01H 5/00* (2006.01)

(52) U.S. Cl.
USPC ..... Plt./376

(58) Field of Classification Search
USPC ..... Plt./376
See application file for complete search history.

*Primary Examiner* — Kent L Bell

(57) ABSTRACT

A new and distinct *Aglaonema* cultivar named 'KKAG201303' is disclosed, characterized by green and yellow-green foliage, decorative green white to white veins, narrow linear leaves and a compact plant shape. The new variety is an *Aglaonema*, typically produced as an indoor ornamental plant.

1 Drawing Sheet

Latin name of the genus and species: *Aglaonema commutatum.*

Variety denomination: 'KKAG201303'.

BACKGROUND OF THE INVENTION

This application relates to a new cultivar of *Aglaonema commutatum*. The new variety is the product of a planned breeding program. The new variety originated as a seedling from the crossing of the unpatented, proprietary seed parent *Aglaonema commutatum* 'BK711' with the unpatented, proprietary pollen parent referred to as *Aglaonema commutatum* 'A848'. The crossing was made by the inventor in a commercial nursery during January of 2005.

The new variety was first selected by the inventor, Kanchana Khemakongkanond, a citizen of Thailand, in March of 2006, at the same nursery in Bangkok, Thailand. After identifying the new variety as a potentially interesting selection, the inventor continued confidential testing and propagation of 'KKAG201303', assessing stability of the unique characteristics of this variety.

Asexual reproduction of the new cultivar 'KKAG201303' by vegetative cuttings was first performed at the same nursery in Bangkok, Thailand during February of 2007. Subsequently at least three generations have been produced from vegetative cuttings, and have shown that the unique features of this cultivar are stable and reproduced true to type.

SUMMARY OF THE INVENTION

The cultivar 'KKAG201303' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KKAG201303'. These characteristics in combination distinguish 'KKAG201303' as a new and distinct *Aglaonema* cultivar:

1. Compact plant shape.
2. Green leaf color with yellow-green margins.
3. Unusual narrow, linear leaves.
4. Decorative green-white to white vein coloration.

PARENT COMPARISON

Plants of the new cultivar 'KKAG201303' are similar to the seed parent, *Aglaonema* 'BK711' in most horticultural characteristics. The new variety, however, produces narrower, shorter leaves with more creamy coloration pattern than those of the seed parent. Additionally the new variety produces a plant of more compact form than the seed parent.

Plants of the new cultivar 'KKAG201303' are similar to the pollen parent, *Aglaonema* 'A848' in most horticultural characteristics. Plants of the new variety, however, produce leaves that are narrower, shorter and show the leaf coloration pattern more clearly than the pollen parent. Additionally the new variety also produces bushier plant growth than the pollen parent.

COMMERCIAL COMPARISON

Plants of the new cultivar 'KKAG201303' are comparable to the unpatented unnamed, *Aglaonema stenophyllum*. The two *Aglaonema* varieties are similar in most horticultural characteristics; however, the new variety 'KKAG201303' produces leaves which are green with creamy white variegation and creamy white petioles. *Aglaonema stenophyllum* produces leaves which are green with yellow variegation and green petioles.

Plants of the new cultivar 'KKAG201303' are comparable to the unpatented variety *Aglaonema* 'Christmas Day'. The two *Aglaonema* varieties are similar in most horticultural characteristics; however, the new variety 'KKAG201303' produces leaves of different shape than those of the comparator 'Christmas Day'. The leaves of the new variety also have a different overall coloration than 'Christmas Day'.

BRIEF DESCRIPTION OF THE PHOTOGRAPH

The accompanying photograph in FIG. 1 illustrates in full color a typical plant of 'KKAG201303' grown in a controlled greenhouse in Honselersdijk, The Netherlands. This plant is approximately 8 months old shown planted in 12 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'KKAG201303' plants grown according to the following protocols.

Plants were grown in Honselersdijk, the Netherlands under controlled greenhouse conditions, with temperatures ranging approximately from 20° C. to 22° C. during the day and 18° C. to 20° C. at night with natural sunlight. Measurements and numerical values below represent averages of typical plant types.

Botanical classification: *Aglaonema commutatum*. 'KKAG201303'.

PROPAGATION

Propagation details:

First propagation method: Cuttings.

Type of propagation typically used: Cuttings.

Time to initiate roots: About 14 days at approximately 21° C.

Root description: Moderately dense, moderately thick, non-fibrous, fleshy, not free-branched, colored greyed-orange; near RHS-CC 165C.

Time to produce rooted plantlet: Approximately 10 weeks at approximately 20 to 22° C.

PLANT

Age of plant described: Approximately 8 months.

Growth habit: Broad upright.

Plant shape: Obovate.

Height: Approximately 14.9 cm to top of highest leaf from soil line.

Plant spread: Approximately 21.3 cm.

Normal pot size: 12 cm pot.

Growth rate: Slow to moderate.

Stem:

- *Diameter*.—1.0 cm.
- *Length*.—4.4 cm.
- *Color*.—Greyed-yellow to greyed-orange; near RHS 162B and 162C, 163B and 163C.
- *Texture*.—Smooth, slightly glossy.

Branching characteristics: Basal branching, emerging from central stem, no lateral branches.

Number of clumps of leaves: 4.

Number of leaves per clump: Average 7, including secondary clumps. Main stem holds an average of 17 leaves.

Number of leaves per plant: Approximately 26 mature leaves.

FOLIAGE

Leaf:

- *Arrangement*.—Scattered.
- *Average length*(*excluding petiole*).—Approximately 11.3 cm.
- *Average width*.—Approximately 1.7 cm.
- *Shape of blade*.—Narrow lanceolate.
- *Aspect*.—Leaves outward (near horizontal).
- *Apex*.—Narrow acute, curled downward.
- *Base*.—Narrow attenuate.
- *Margin*.—Entire.
- *Texture of top surface*.—Smooth.
- *Texture of bottom surface*.—Smooth.
- *Appearance of top surface*.—Moderately glossy.
- *Appearance of bottom surface*.—Slightly glossy.
- *Color*.—Young foliage upper side: Green; near in between RHS 137A and 143A, closest to 137A, narrowly margined yellow-green; near RHS 150D, veined yellow-green; 145C and 145D. Young foliage under side: Green to yellow-green; near in between RHS 138A and 146B, narrowly margined yellow-green; near RHS 145D and 150D, veined yellow-green; 145C. Mature foliage upper side: Green to yellow-green; near in between RHS 139A and 147A, closest to 139A but considerably darker. Narrowly margined yellow-green and green-white; near RHS 150D and 157B. Mature foliage under side: Green; near RHS 137A, finely marbled lighter; near RHS 138C, narrowly margined yellow-green and green-white; near RHS 150D and 157B.

Venation:

- *Type*.—Pinnate.
- *Venation coloration upper side*.—Main vein green-white; near RHS 157A, 157B and 157C, main vein margined yellow-green; 150A, secondary veins green-white; near RHS 157A to 157C, margined greyed-green; N189C.
- *Venation coloration under side*.—White; near RHS NN155A.

Sheath:

- *Average length*.—Approximately 4.2 cm.
- *Average width*.—Approximately 0.3 cm.
- *Color*.—White; near RHS NN155B and NN155C.
- *Texture*.—Smooth.
- *Appearance*.—Slightly glossy.

Petiole (excluding geniculum):

- *Length*.—Approximately 4.3 cm.
- *Width*.—At distal end: Approximately 0.3 cm. Above clump: Approximately 0.6 cm.
- *Color*.—White; near RHS NN155B to NN155C.
- *Strength*.—Moderately strong.

Geniculum:

*Length*.—Approximately 0.7 cm.

*Width*.—Approximately 0.3 cm.

*Color*.—White; near RHS NN155B and NN155C.

FLOWERING CHARACTERISTICS

Flowering not observed to date.

REPRODUCTIVE ORGANS

Not observed to date

OTHER CHARACTERISTICS

Disease resistance: Good resistance to the normal diseases found in *Aglaonema*.

Drought tolerance and cold tolerance: Normal for species, USDA zone 10 and higher.

Fruit/seed production: No fruits/seeds detected to date.

What is claimed is:

1. A new and distinct cultivar of *Aglaonema* plant named 'KKAG201303' as herein illustrated and described.

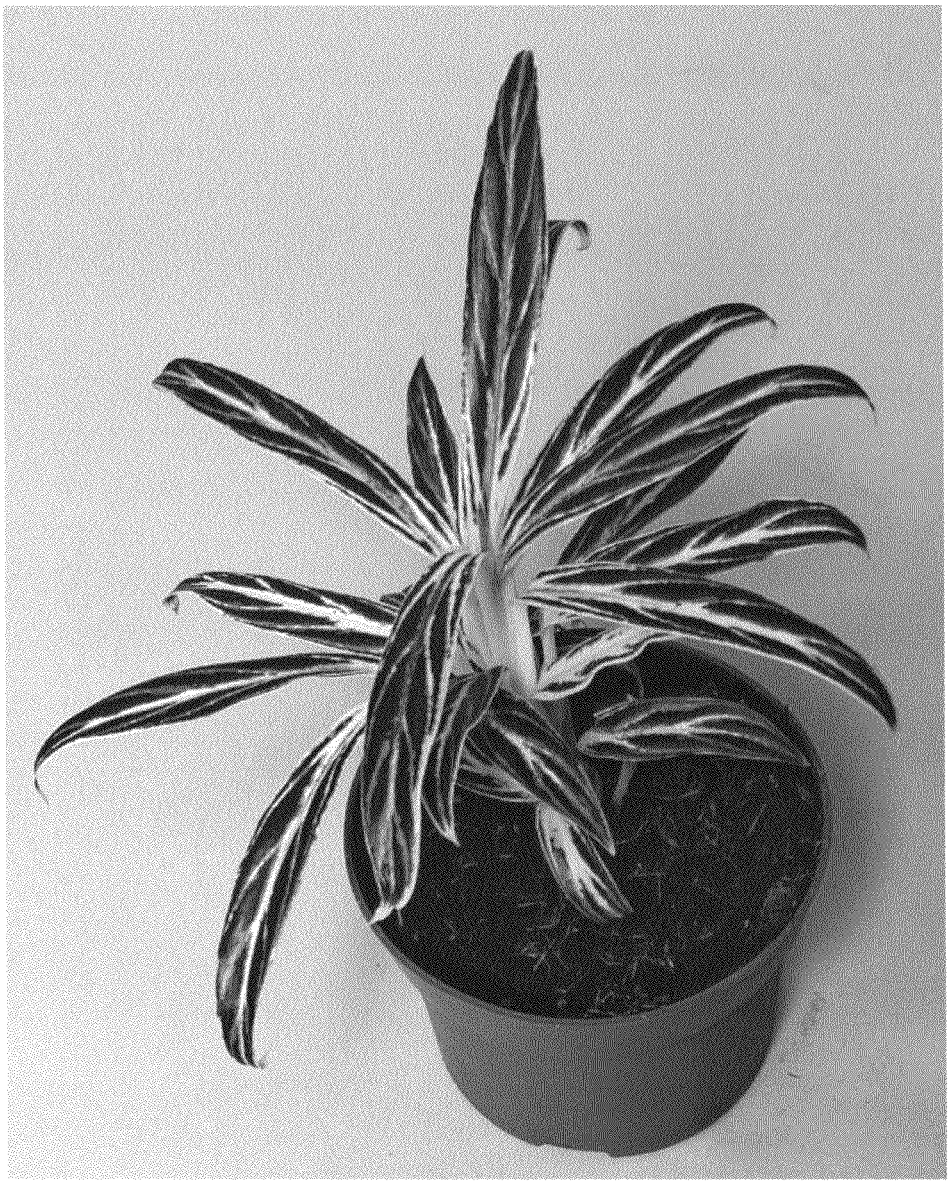

* * * * *